US006436892B1

(12) United States Patent
Leonard et al.

(10) Patent No.: US 6,436,892 B1
(45) Date of Patent: Aug. 20, 2002

(54) CLEANING WIPE COMPRISING 2 BROMO-2 NITROPROPANE-1,3 DIOL

(75) Inventors: Isabelle Leonard, Voroux-lez-Liers; Didier Dormal, Aywaille; Jean Julemont, Verviers, all of (BE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/016,275

(22) Filed: Dec. 10, 2001

Related U.S. Application Data

(63) Continuation-in-part of application No. 09/904,342, filed on Jul. 12, 2001, now Pat. No. 6,346,506.

(51) Int. Cl.[7] .............................................. C11D 17/00

(52) U.S. Cl. ........................ 510/438; 510/439; 510/295; 510/499; 510/505; 510/506; 134/42; 428/288; 15/209.1

(58) Field of Search ................................. 510/438, 439, 510/295, 499, 505, 506; 134/42; 428/288; 15/209.1

(56) References Cited

U.S. PATENT DOCUMENTS 5,141,803 A * 8/1992 Pregozen .................... 428/288
6,284,259 B1 * 9/2001 Beerse et al. ............... 424/404
6,340,663 B1 * 1/2002 Deleo et al. ................. 510/438

* cited by examiner

*Primary Examiner*—Necholus Ogden
(74) *Attorney, Agent, or Firm*—Richard E. Nanfeldt

(57) ABSTRACT

A cleaning wipe comprising a nonwoven fabric wherein the nonwoven fabric is impregnated with a cleaning composition.

4 Claims, No Drawings

CLEANING WIPE COMPRISING 2 BROMO-2 NITROPROPANE-1,3 DIOL

RELATED APPLICATION

This application is a continuation in part of U.S. Ser. No. 09/904,342 filed Jul. 12, 2001 now U.S. Pat. No. 6,346,506.

FIELD OF INVENTION

The present invention relates to a nonwoven fabric which has been impregnated with a liquid cleaning composition.

BACKGROUND OF THE INVENTION

The patent literature describes numerous wipes for both body cleaning and cleaning of hard surfaces but none describe the instant cleaning wipes which have improved cleaning characteristics in the minimization of streaking and residue.

U.S. Pat. Nos. 5,756,612; 5,763,332; 5,908,707; 5,914,177; 5,980,922 and 6,168,852 teach cleaning compositions which are inverse emulsions.

U.S. Pat. Nos. 6,183,315 and 6,183,763 teach cleaning compositions containing a proton donating agent and having an acidic pH.

U.S. Pat. Nos. 5,863,663; 5,952,043; 6,063,746 and 6,121,165 teaches cleaning compositions which are out in water emulsions.

SUMMARY OF THE INVENTION

A cleaning wipe for cleaning hard surfaces such as walls, counter tops and floors comprises a nonwoven fabric containing at least polyester fibers and viscose fibers, wherein is the nonwoven fabric is impregnated with a liquid cleaning composition containing a zwifterionic surfactant, at least one nonionic surfactant, a disinfecting agent, a cosurfactant, an alkanol, optionally, an anionic surfactant, optionally, a proton donating agent and water, wherein the liquid cleaning composition is not an emulsion and does not contain proteins, metallic salts, enzymes, amides, sodium hypochlorite, dimethicone, N-methyl-2-pyrrolidone, monoalkyl phosphate or silicon based sulfosuccinate.

DETAILED DESCRIPTION OF THE INVENTION

The present invention relates to an antibacterial cleaning wipe for hard surfaces which comprises approximately:

(a) 20 wt. % to 30 wt. % of a nonwoven fabric which consists of at least polyester fibers and viscose fibers and preferably consists of 60 wt. % to 95 wt. % of wood pulp fibers, 2.5 wt. % to 20 wt. % of viscose fibers and 2.5 wt. % to 20 wt. % of polyester fibers; and (b) 70 wt. % to 80 wt. % of a liquid cleaning composition being impregnated in said nonwoven fabric, wherein said liquid cleaning composition comprises:

(i) 0.1 wt. % to 10 wt. %, more preferably 0.25 wt. % to 8 wt. % of a zwitterionic surfactant;

(ii) 0 to 6 wt. %, more preferably 0.25 wt. % to 4 wt. % of a $C_1$–$C_4$ alkanol;

(iii) 1 wt. % to 10 wt. %, more preferably 1.5 wt. % to 8 wt. % of a blend of water soluble glycol ethers;

(iv) 0 to 4 wt. %, more preferably 0.1 wt. % to 1 wt. % of a disinfecting agent such as a perfume, essential oil or triclosan;

(v) 0.5 wt. % to 10 wt. % of a nonionic surfactant formed from a $C_8$–$C_{18}$ alkanol and about 6 to about 9, preferably about 7 to about 8.5 moles of ethylene oxide;

(vi) 0.1% to 4% of an ethoxylated nonionic surfactant formed from a $C_9$–$C_{11}$ alkanol and about 2 to about 3 moles of ethylene oxide;

(vii) 0 to 6 wt. %, more preferably 0.1 wt. % to 5 wt. % of an anionic surfactant;

(viii) 0 to 0.2 wt. %, more preferably 0.05 wt. % to 0.2 wt. % of a proton donating agent;

(ix) 0 to 0.3 wt. %, more preferably 0.05 wt. % to 0.2 wt. % of an alkali metal hydroxide such as sodium hydroxide and/or potassium hydroxide;

(x) 0.01 wt. % to 0.1 wt. % of a preservative such as 2bromo-2nitro propane-1,3 diol; and (xi) the balance being water, wherein the composition has a pH of about 5.25 to about 7.

The water-soluble zwitterionic surfactant (betaine), which is used in the instant cleaning composition and provides good foaming properties and mildness to the composition. The zwitterionic surfactant is a water soluble betaine having the general formula:

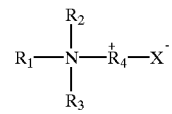

wherein X− is selected from the group consisting of $SO_3$− and $CO_2$− and $R_1$ is an alkyl group having 10 to about 20 carbon atoms, preferably 12 to 16 carbon atoms, or the amido radical:

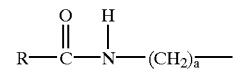

wherein R is an alkyl group having about 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyidimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc. The instant compositions show a marked improvement in ecotoxocity as compared to existing commercial products.

The water soluble nonionic surfactants utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_9$–$C_{11}$ alkanol condensed with 2.5 to 10 moles of ethylene oxide (NEODOL 91-2.5 or -5 or -6 or -8), $C_{12\text{-}13}$ alkanol condensed with 6.5 moles ethylene oxide (Neodol 23-6.5), $C_{12}$-$_{15}$ alkanol condensed with 12 moles ethylene oxide (Neodol 25-12), $C_{14}$-$_{15}$ alkanol condensed with 13 moles ethylene oxide (Neodol 45-13), and the like.

An especially preferred nonionic system comprises the mixture of a nonionic surfactant formed from a $C_9$–$C_{11}$ alkanol condensed with 2 to 3.5 moles of ethylene oxide ($C_{9-11}$ alcohol EO 2 to 3.5:1) with a nonionic surfactant formed from a $C_9$–$C_{11}$ alkanol condensed with 7 to 9 moles of ethylene oxide ($C_9$–$C_{11}$ alcohol EO 7 to 9:1), wherein the weight ratio of the $C_9$–$C_{11}$ alcohol EO 7 to 9:1 to the $C_9$–$C_{11}$ alcohol EO 2 to 3.5:1 is from 8:1 to 1:1 from preferably 6:1 to 3:1.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Also among the satisfactory nonionic detergents are the water-soluble condensation products of a $C_8$–C20 alkanol with a heteric mixture of ethylene oxide and propylene oxide wherein the weight ratio of ethylene oxide to propylene oxide is from 2.5:1 to 4:1, preferably 2.8:1 to 3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$–C20 alkanoic acid esters having a HLB of 8 to 15 also may be employed as the nonionic detergent ingredient in the described composition. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic detergents are marketed under the trade name "Pluronics". The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

The preferred anionic surfactant used in the instant composition is a paraffin sulfonates containing 10 to 20, preferably 13 to 17 carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503, 280; 2,507,088; 3,260,744; 3,372,188 and German Patent 735,096.

The cosurfactants in the instant compositions are selected from the group consisting of polypropylene glycol of the formula $HO(CH_3CHCH_2O)_nH$ wherein n is a number from 1 to 18, and mono and di $C_1$–$C_6$ alkyl ethers and esters of ethylene glycol and propylene glycol having the structural formulas $R(X)_nOH$, $R_1(X)_nOH$, $R(X)_nOR$ and $R_1(X)_nOR_1$ wherein R is $C_1$–$C_6$ alkyl group, $R_1$ is $C_2$–$C_4$ acyl group, X is $(OCH_2CH_2)$ or $(OCH_2(CH_3)CH)$ and n is a number from 1 to 4, diethylene glycol, triethylene glycol, an alkyl lactate, wherein the alkyl group has 1 to 6 carbon atoms, 1 methoxy-2-propanol, 1 methoxy-3-propanol, and 1 methoxy 2-, 3- or 4-butanol.

Representative members of the polypropylene glycol include dipropylene glycol and polypropylene glycol having a molecular weight of 150 to 1000, e.g., polypropylene glycol 400. Satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether, mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate. While all of the aforementioned glycol ether compounds provide the described stability, the most preferred cosurfactant is propylene glycol N-butyl ether.

The preferred $C_1$–$C_4$ alkanols are ethanol or isopropanol and mixtures thereof.

The proton donating agent that can be used in the instant composition is selected from the group consisting of organic acids and inorganic acids and mixtures thereof. The organic acids are selected from the group consisting of mono- and di-aliphatic carboxylic acids and hydroxy containing organic acids and mixtures thereof. Typical organic acids are adipic acid, succinic acid, lactic acid, glycolic acid, salicylic acid, tartaric acid and ortho hydroxy benzoic acid. Typical inorganic acids are sulfuric acid, nitric acid and hydrochloric acid.

The final essential ingredient in the instant composition is water. The proportion of water in the compositions generally is in the range of 70 wt. % to 98.5 wt. %.

The cleaning composition of this invention may, if desired, also contain other components either to provide additional effect or to make the product more attractive to the consumer. The following are mentioned by way of example: Colors or dyes in amounts up to 0.5% by weight; preservatives or antioxidizing agents, such as iodo propynyl butyl carbamate, formalin, 5-bromo-5-nitro-dioxan-1,3; 5-chloro-2-methyl-4-isothaliazolin- 3-one, 2,6-di-tert.butyl-p-cresol, etc., in amounts up to 2% by weight; and pH adjusting agents, such as sulfuric acid or sodium hydroxide, as needed.

The cleaning compositions are prepared by simple batch mixing at 25° C.–30° C. The nonwoven fabric is impregnated with the liquid cleaning composition by means of a positive impregnation process. The liquid is positively fed into the nonwoven fabric through a controlled gear pump and injection bar at a ratio of about 2.5 to 3 grams of liquid cleaning composition to about 1 gram of the nonwoven fabric.

The nonwoven fabric is formed from 10 wt. % to 90 wt. % of viscose fibers and 10 wt. % to 90 wt. % of polyester fibers such as Spunlace made by the Dexter Corporation. More preferably the nonwoven fabric comprises 10 wt. % to 95 wt. % of wood pulp fibers, 1 wt. % to 40 wt. % of viscose fibers and 1 wt. % to 40 wt. % of polyester fibers. Such a nonwoven fabric which is manufactured by Dexter Corporation under the name Hydraspun comprises about 60% to 95% of wood pulp fabrics, 2.5 wt. % to 20 wt. % of viscose fibers and 2.5 wt. % to 20 wt. % of polyester fibers.

The following examples illustrate liquid cleaning compositions of the described invention. The exemplified compositions are illustrative only and do not limit the scope of the invention. Unless otherwise specified, the proportions in the examples and elsewhere in the specification are by weight.

The following cleaning wipes were made by the aforementioned process.

|  | A Wt. % | B Wt. % |
|---|---|---|
| Part I |  |  |
| Dipropylene glycol N-butyl ether | 2 | 1 |
| Ethanol | 2 | 4 |
| Cocoamido propyl dimethyl betaine 30% | 2 | 3 |
| C9–C11 alcohol EO7.5–8:1 nonionic | 1.5 | 3 |
| Perfume | 0.1 | 0.1 |
| C9–C11 alcohol EO2.5:1 nonionic | 0.2 | 0.3 |
| Citric acid monohydrate | 0.15 | 0.12 |
| Propylene glycol monobutyl ether | 1 | 2 |
| NaOH 50% | 0.14 | 0.14 |
| 2bromo2-nitropropane-1,3diol | 0.02 | 0.02 |
| Water | Bal | Bal |
| Part II |  |  |
| Part I | 73.68 | 73.68 |
| Spunlace | 26.32 |  |
| Hydraspun 8579 |  | 26.32 |

Formulas A and B were tested for cleaning performance on Perspex tiles and rated on a 10 point scale (0=very poor/much residue and 10=very good/no residue).

|  | A | B |
|---|---|---|
| Residue score | 2.3 | 2.4 |

15 cm×15 cm Perspex black tiles are wiped with the impregnated test substrate in a circular movement such that the middle of the tile is wet and contours kept dry.

Each test product is applied on 5 different tiles (=5 replicates), then 5 judges score the residue pattern (observation made under indirect light conditions) of each tile from 0=very poor residue score up to 10=excellent, no residue on a 10 point scale. Results are then analyzed statistically.

What is claimed:

1. A hard surface cleaning wipe which comprises approximately:
   (a) 20 wt. % to 30 wt. % of a nonwoven fabric; and
   (b) 70 wt. % to 80 wt. % of a liquid cleaning composition being impregnated in said nonwoven fabric, wherein said liquid cleaning composition comprises:
      (i) 0.05% to 0.2% of a proton donating agent,
      (ii) 0.19 to 4% of at least one disinfecting agent;
      (iii) 0.5 to 10% of an ethoxylated nonionic surfactant formed from a $C_9$–$C_{11}$ alkanol and about 6 to about 9 moles of ethylene oxide;

(iv) 0.1% to about 4.0% of an ethoxylated nonionic surfactant formed from a $C_9$–$C_{11}$ alkanol and about 2 to about 3 moles of ethylene oxide;
(v) 0.1% to 10% of an surfactant;
(vi) 0.01% to 0.1% of 2 bromo-2 nitro propane-1,3 diol;
(vii) 0.05 to 0.3% of an alkali metal hydroxide;
(viii) 1.0% to 10% of a blend of glycol ethers consisting of propylene glycol N-butly ether and dipropylene glycol N-butyl ether.
(ix) about 2% by weight of a preservative selected from the group consisting of 5-bromo-5-nitro-diocan-1,3 and 5-chloro-2-methyl-4-isothaliazlin-3-one;
(x) pH of 5.25 to 7.0; and
(xi) the balance being water.

2. The cleaning wipe of claim 1, wherein said zwitteronic surfactant is a cocoamidopropyl dimethyl betaine.

3. The cleaning wipe of claim 2, further including a $C_1$–$C_4$ alkanol is ethanol or isopropanol.

4. The cleaning wipe of claim 1, further including an anionic surfactant.

* * * * *